(12) United States Patent
Bentley

(10) Patent No.: US 6,394,604 B1
(45) Date of Patent: May 28, 2002

(54) DEVICE AND METHOD FOR IN-VITRO EXAMINATION OF AN ENUCLEATED EYE

(75) Inventor: Joseph R. Bentley, West Jordan, UT (US)

(73) Assignee: Bausch & Lomb Inc., Rochester, NY (US)

( * ) Notice: Subject to any disclaimer, the term of this patent is extended or adjusted under 35 U.S.C. 154(b) by 108 days.

(21) Appl. No.: 09/599,247

(22) Filed: Jun. 22, 2000

(51) Int. Cl.⁷ .................................................. A61B 3/00
(52) U.S. Cl. ...................................................... 351/245
(58) Field of Search ................................ 351/200, 205, 351/245, 246; 606/166, 4, 5; 623/4.1, 5.11, 5.14, 6.12; 206/5, 5.1; 220/345.1, 345.2, 345.4; 356/244, 246

(56) References Cited

U.S. PATENT DOCUMENTS

| | | | | | |
|---|---|---|---|---|---|
| 4,187,005 A | * | 2/1980 | Rosenberger | ................ | 351/245 |
| 4,269,307 A | * | 5/1981 | LaHaye | ....................... | 206/5.1 |
| 4,744,362 A | * | 5/1988 | Grundler | ..................... | 606/166 |

* cited by examiner

Primary Examiner—George Manuel
(74) Attorney, Agent, or Firm—Michael L. Smith

(57) ABSTRACT

An enucleated eye examination container 10 includes a housing 12 with an interior 14 to be pressurized. An eye retaining member 16 is contained within housing 12. An eye abutment portion 18 receives the eye 20 so that the eye 20 is urged against eye abutment portion 18 by eye retaining member 16. A connector 24 is attached to housing 12 for connection to a pressurized source of gas.

11 Claims, 3 Drawing Sheets

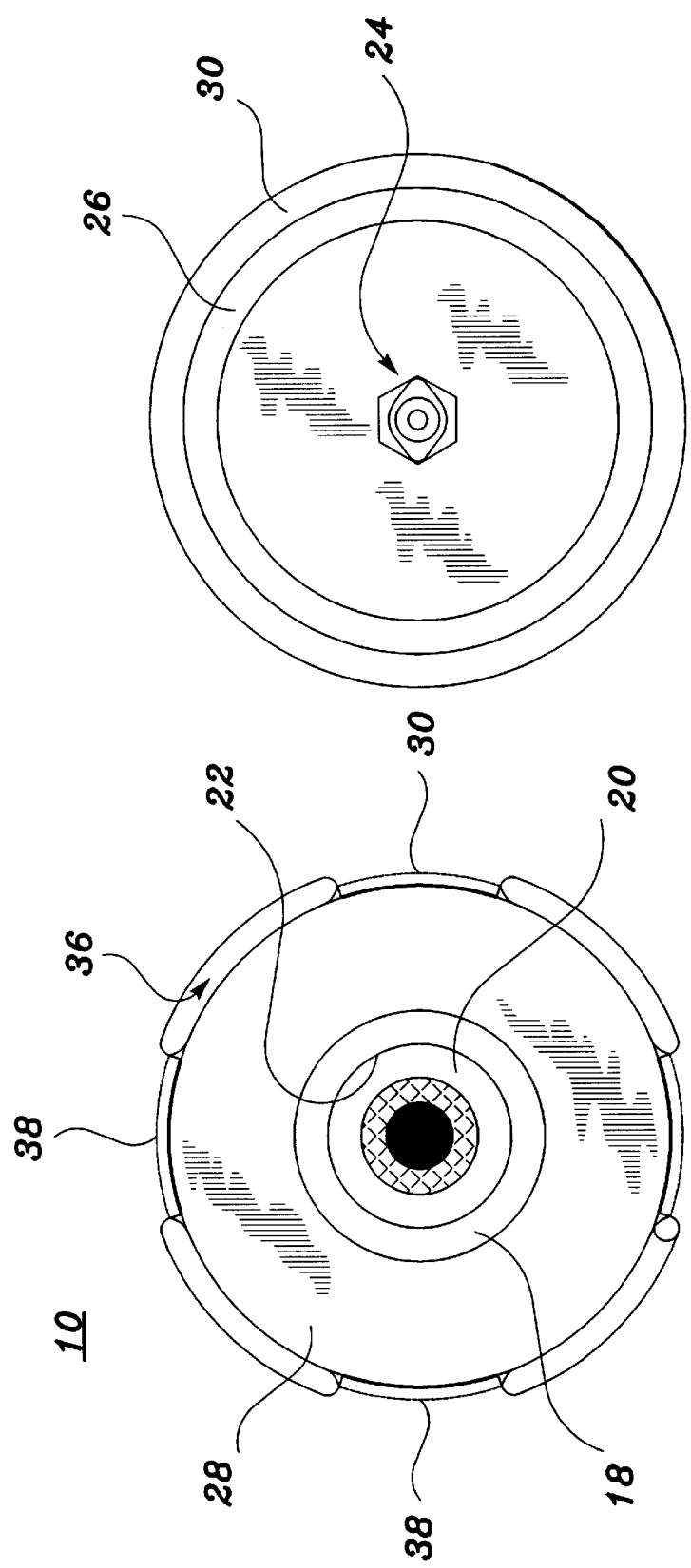

DEVICE AND METHOD FOR IN-VITRO EXAMINATION OF AN ENUCLEATED EYE

BACKGROUND OF THE INVENTION

1. Field of the Invention

The present invention relates to a device and method for securing an enucleated eye to allow examination of the eye. More particularly, the present invention relates to a device enabling the enucleated eye to be pressurized to allow for accurate examination of the eye.

2. Description of Prior Art

Enucleated donor eyes are used for harvesting corneas for transplant procedures. The optical properties and physical characteristics of the cornea must be established before harvesting a cornea for a transplant procedure. Enucleated eyes typically have low intraocular pressure. Therefore, the intraocular pressure needs to be increased in order to allow proper examination of the cornea of the enucleated eye.

A typical prior art solution to this problem is the insertion of saline solution into the eye to increase the pressure. This solution however is less than desirable because the process of pressurizing the enucleated eye involves an invasive procedure and the method of mounting the eye by clamping to the optic nerve, which is pulled into a ring, is difficult and time consuming. Another method used is to simply hold the eye by hand while it is examined.

Thus, there is a need to permit an accurate, detailed analysis of the enucleated eye in conditions similar to in-vivo in an aseptic environment.

BRIEF DESCRIPTION OF THE DRAWINGS

FIG. 2 is a front elevation of FIG. 1;

FIG. 3 is a rear elevation of FIG. 1; and

DETAILED DESCRIPTION OF THE PREFERRED EMBODIMENTS

An enucleated eye examination container includes a housing with an interior to be pressurized, an eye retaining member disposed within the housing, an eye abutment portion for receiving the eye, and a connector attached to the housing for connection to a pressurized source of gas for pressurizing the eye.

Figure 1:
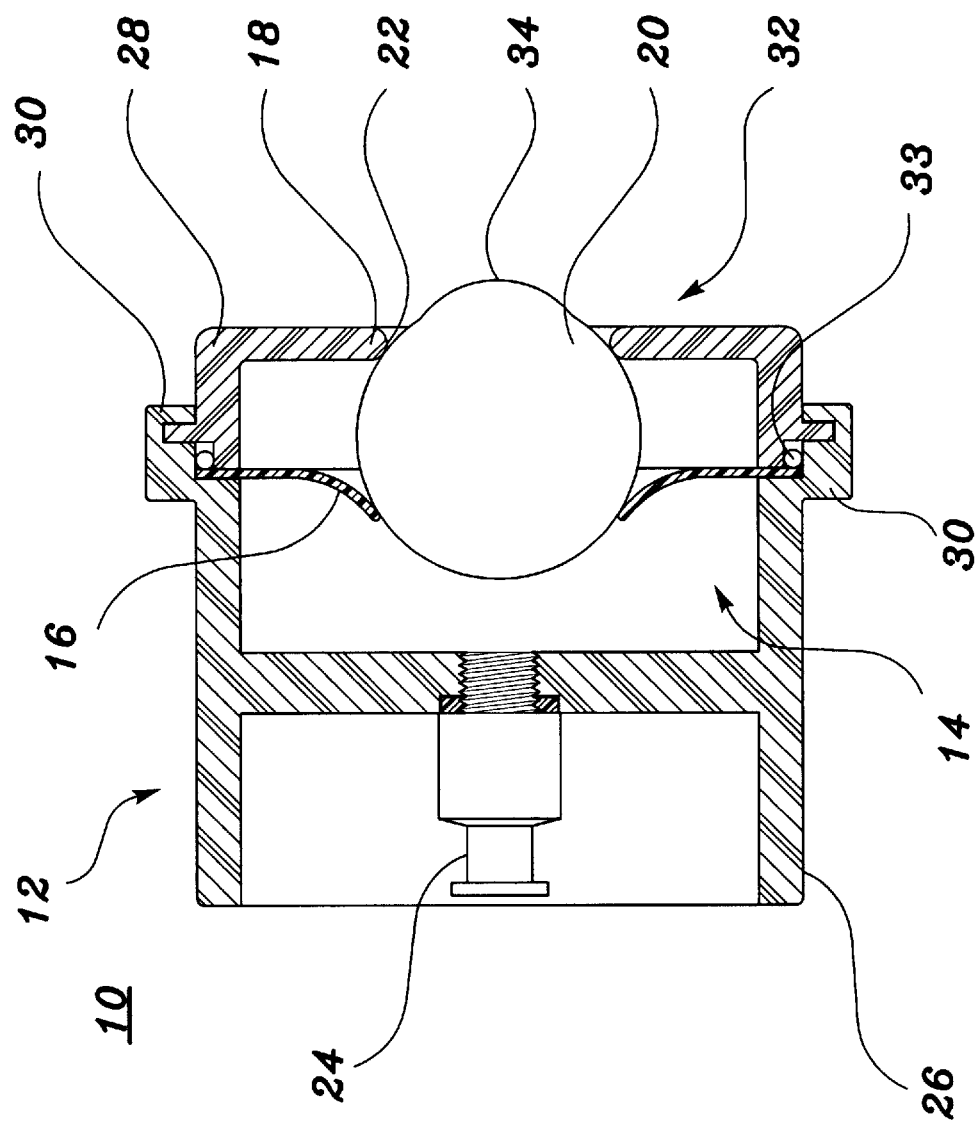
FIG. 1 is a cross-section of a device in accordance with the present invention.

FIG. 1 shows a cross-sectional view of an enucleated eye examination container 10 in accordance with the present invention. Container 10 includes a housing 12 having an interior 14 to be pressurized. Housing 12 is preferably made of ABS or any of a number of medically approved transparent plastics with suitable mechanical properties. Housing 12 is preferably transparent so that a user can be sure the eye to be examined is properly positioned within container 10.

Disposed within housing 12 is an eye retaining member 16. Eye retaining member 16 is preferably constructed of flexible resilient material such as polyethylene.

In use, eye abutment portion 18 receives an eye 20 such that the eye 20 is urged against the abutment portion 18 by eye retaining member 16 to form a seal at 22.

A connector 24 is attached to housing 12 for connection to a pressurized source of gas (not shown) for pressurizing the eye 20 for maintaining the natural shape of the eye 20 to allow the eye 20 to be accurately examined. Preferably, the housing is pressurized to approximately 4 inches of water. The source of gas is preferably air or some inter-gas such as nitrogen.

Housing 12 preferably includes a main body portion 26 and an eye cap portion 28. Main body portion 26 includes an integral annular ring 30 for removably attaching eye cap portion 28 to the main body portion 26. The main body portion includes a resilient member 16 and a connector 24. Eye cap portion 28 is removably attached to the main body portion 26 and includes the eye abutment portion 18 which is attached at an aperture 32 for receiving eye 20 such that a cornea 34 may be examined. It is noted that in order to enhance the seal at 22, a gasket (not shown) may be attached at aperture 32. O-ring 33 ensures that a seal is formed between main body 26 and eye cap portion 28. In. pressurizing container 10 the objective is to pressurize eye 20 so that it is in a natural state as close to an in-vivo condition as possible. This pressurization allows accurate examination of eye 20.

Referring to FIG. 2, container 10 preferably includes eye cap portion or cover 28 removably attached to main body 26 and annular ring 30 via a bayonet-type connection. Annular ring 30 preferably includes slots 36 for receiving tabs 38 (shown by the dotted lines in FIG. 2). In order to attach cover 28 to annular ring 30, tabs 38 are placed within slots 36 and then cover 28 is rotated to the position shown in FIG. 2. Cover 28 is preferably removably and sealably attached to the main body 26 such that together the cover 28 and main body 26 form a housing 12. Eye retaining member 16 and eye abutment portion 18 together form eye securing apparatus that is disposed within the main body and the cover for securing the eye 20 in a fixed position.

FIG. 3 shows a rear elevation of container 10 including connector 24, main body 26, and annular ring 30.

Figure 4:
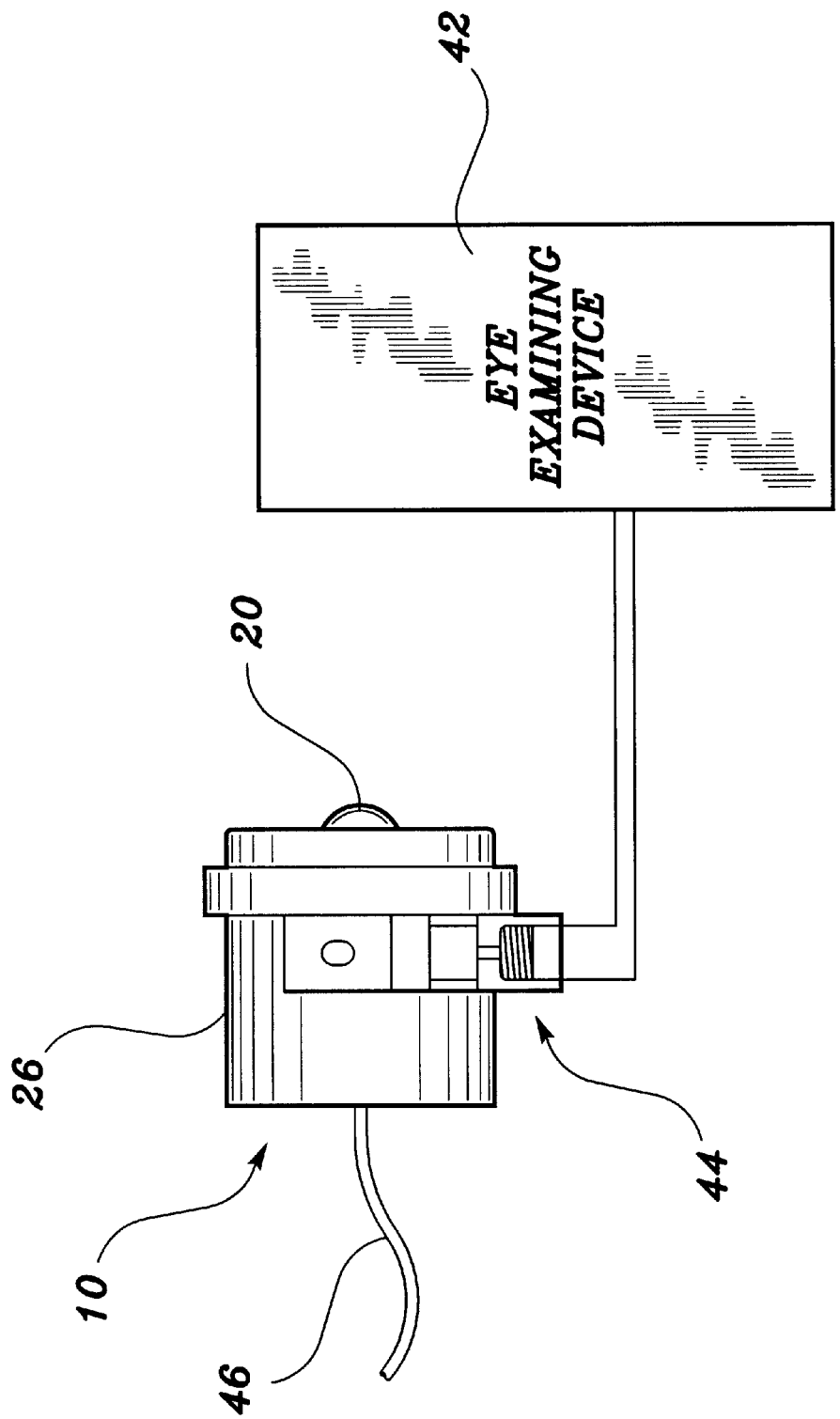
FIG. 4 is an illustration of an enucleated eye examination system in accordance with the present invention.

FIG. 4 shows an examination system 40, in accordance with the present invention, and includes container 10, which is capable of being pressurized and secures the eye 20 in a fixed. position. System 40 further includes an eye examining device 42 such as an OBSCAN II unit available from Bausch & Lomb, Inc. or any of many other known eye examining devices such as ultrasonic devices, wavefront sensors, or other well-known devices. Preferably, system 40 includes a bracket 44 for holding the container 10 such that the eye examining device 42 can examine the eye 20. Gas line 46 is connected to a source of pressurized gas, as described above. In use, container 10 secures eye 20 in a fixed position. Eye 20 is then pressurized to maintain a natural shape allowing for accurate examination of eye 20. Container 10 is then mounted in association with eye examining device 42 so that eye 20 can be examined.

Thus, there has been shown and described an inventive device and method for examining an enucleated eye. Other embodiments of the present invention will be readily apparent to those skilled in the art and should be considered within the scope of the present invention. For instance, eye retaining member 16 may take on many possible constructions. For example, eye retaining member 16 may be a continuous resilient membrane or it could be formed of a plurality of fins or be a series of straps. The purpose of eye retaining member 16 is to urge eye 20 into sealing contact with eye abutment portion 18 and still allow eye 20 to be pressurized.

What is claimed is:

1. An enucleated eye examination container comprising:

a housing having an interior to be pressurized;

an eye retaining member disposed within the housing;

an eye abutment portion for receiving the eye such that the eye is urged against the abutment portion by the eye retaining member; and a connector attached to the housing for connection to a pressurized source of gas for pressurizing the eye for maintaining a natural shape of the eye to allow the eye to be accurately examined.

2. The container for claim 1 wherein the housing interior is pressurized to approximately 4 inches of water.

3. The container of claim 1 wherein the housing is formed of a transparent plastic.

4. The container of claim 1 the housing further including:

a main body portion wherein the main body portion includes the eye retaining member and the connector; and an eye cap portion removably attached to the main body portion and including the eye abutment portion.

5. The container of claim 1 wherein the eye retaining member is formed of a transparent plastic.

6. An enucleated eye examination container comprising:

a main body;

a cover removably and sealably attached to the main body such that together the cover and main body form a housing;

eye securing apparatus disposed within the housing for securing the eye in a fixed position; and a connector attached to the housing for connection to a pressurized gas source.

7. The container of claim 6 wherein the housing interior is pressurized to approximately 4 inches of water.

8. The container of claim 6 wherein the eye securing apparatus includes an eye retaining member disposed within the housing and an eye abutment portion for receiving the eye such that the eye is urged against the abutment portion by the eye retaining member.

9. An enucleated eye examination system comprising:

a container capable of being pressurized and for securing the eye in a fixed position;

an eye examining device; and a bracket for holding the container such that the eye examining device can examine the eye.

10. The system of claim 9, the container further including:

a housing having an interior to be pressurized;

an eye retaining member disposed within the housing;

an eye abutment portion for receiving the eye such that the eye is urged against the abutment portion by the eye retaining member; and a connector attached to the housing for connection to a pressurized source of gas for pressurizing the housing interior.

11. A method of examining an enucleated eye comprising the steps of:

providing a container and securing the eye in a fixed position;

pressurizing the eye to ensure that the eye maintains a natural shape to allow for accurate examination of the eye; and mounting the container in association with an eye examining device so that the eye can be examined.

\* \* \* \* \*